United States Patent [19]

Barwick

[11] Patent Number: 5,041,092

[45] Date of Patent: Aug. 20, 1991

[54] URETHRAL INDWELLING CATHETER WITH MAGNETICALLY CONTROLLED DRAINAGE VALVE AND METHOD

[75] Inventor: Carl Barwick, Caledonia, Wis.

[73] Assignee: Medical Engineering Corporation, Racine, Wis.

[21] Appl. No.: 608,605

[22] Filed: Oct. 30, 1990

Related U.S. Application Data

[63] Continuation of Ser. No. 400,194, Aug. 29, 1989, abandoned.

[51] Int. Cl.$^5$ .................. A61M 29/00; A61F 2/00
[52] U.S. Cl. ................... 604/104; 604/246; 128/DIG. 25; 600/29
[58] Field of Search .............. 604/8, 9, 65, 96, 97, 604/99, 101, 246, 247, 280; 128/DIG. 25; 600/12, 29–31; 251/65

[56] References Cited

U.S. PATENT DOCUMENTS

| | | | |
|---|---|---|---|
| 3,354,898 | 11/1967 | Barnes | 251/65 |
| 3,419,008 | 12/1968 | Plishner | 251/65 |
| 3,503,400 | 3/1970 | Ostagen et al. | 128/DIG. 25 |
| 3,642,004 | 2/1972 | Ostagen et al. | 128/DIG. 25 |
| 3,731,670 | 5/1973 | Loe | 600/30 |
| 3,812,841 | 5/1974 | Isaacson | 128/DIG. 25 |
| 4,850,963 | 7/1989 | Sparks et al. | 128/DIG. 25 |
| 4,932,938 | 6/1990 | Goldberg et al. | 604/96 |

FOREIGN PATENT DOCUMENTS

| | | | |
|---|---|---|---|
| 2537506 | 3/1977 | Fed. Rep. of Germany | 128/DIG. 25 |
| 1194358 | 6/1970 | United Kingdom | 600/30 |

*Primary Examiner*—John D. Yasko
*Assistant Examiner*—Anthony Gutowski
*Attorney, Agent, or Firm*—S. Krieger

[57] ABSTRACT

The catheter includes a user controlled incontinence portion that is combinable with a combination inflation/drainage member. The inflation/drainage member can be detached from the incontinence portion to provide a user controlled device. A magnetic valve is incorporated in the user controlled incontinence portion for magnetic actuation with an external magnet. The valve is normally closed and magnetically actuatable to an open condition. Removal of the external magnet from proximity to the penis enables the valve to assume its normally closed position. In one embodiment of the invention the valve includes a pressure relief feature. In another embodiment of the invention there is no pressure relief feature.

18 Claims, 5 Drawing Sheets

URETHRAL INDWELLING CATHETER WITH MAGNETICALLY CONTROLLED DRAINAGE VALVE AND METHOD

This is a continuing application of application Ser. No. 400,194 filed Aug. 29, 1989, now abandoned.

BACKGROUND OF THE INVENTION

This invention relates to user controlled incontinence devices for males and more particularly to an indwelling catheter with a magnetically operable drainage valve.

Male urinary incontinence is a common problem that can arise from muscle weakness, post-operative surgical damage to the urinary sphincter or a variety of other debilitating problems. Thus far there have been no satisfactory surgical procedures for correcting incontinence to the extent that bladder control is substantially restored.

Some known devices that deal with the problem of male incontinence include a urethral catheter that allows the bladder to continuously drain into a collection bag without enabling the user to control urinary discharge. Such devices thus limit the physical activity of the user.

Other known devices which address the problem of male incontinence attempt some form of drainage control and include user controlled valves, such as shown in U.S. Pat. Nos. 3,331,371; 3,768,102; 4,026,298 and 4,350,161.

The foregoing patents require manipulation of a valve through the penis in order to place the valve in an open position to permit urinary flow. Occasionally the manipulation of the penis that is intended to actuate a valve into an open position to permit urinary discharge may cause pain or may constrict the urethral passage and impede bladder drainage.

U.S. Pat. No. 3,812,841 shows a magnetically controlled valve installed near the bladder. The valve is actuated into an open condition by an external battery powered magnetic activating device packaged in a relatively large housing making it cumbersome and unwieldy to use. Such device inhibits the activity of the user since it is necessary to have access to the magnetic actuator in order to drain the bladder. The user must thus carry the magnetic activator with him at all times or confine his activities to a location where a magnetic activator is available for use. U.S. Pat. No. 3,495,620 also shows a magnetic valve arrangement requiring external actuation of the valve by a battery powered magnetic activator.

U.S. Pat. No. 3,731,670 shows a magnetically activated binary duct valve with two valve seats that respectively correspond to open and closed positions of the valve. The valve is actuated by an external magnet into the open or closed position. However there is no automatic shutoff of fluid flow when urinary discharge is completed. Thus a user may inadvertently forget to actuate the valve from its open position to its closed position. A further problem is that the user may be unable to detect when he has actuated the valve into a closed position, and may think he has the valve in a closed position while it is actually in an open position.

U.S. Pat. Nos. 3,419,008; 3,926,175; 3,939,821 and 4,024,855 relate to magnetically actuated valve clamps that pinch or clamp a body passage, such as a urethra, into a closed condition. Such devices require surgical implantation of a clamping device and cannot be easily removed for repair or replacement.

It is thus desirable to provide a user controlled incontinence device having a drainage valve which can be actuated without manipulation, without batteries, wiring arrangements or other bulky, cumbersome accessories that inhibit the activity of the user. It is further desirable to provide a user controlled incontinence device which is magnetically actuatable to an open position to permit urinary drainage and automatically reverts to a closed position when the magnetic actuation is removed.

OBJECTS AND SUMMARY OF THE INVENTION

Among the several objects of the invention may be noted the provision of a novel indwelling urethral catheter with incontinence control, a novel indwelling urethral catheter having a magnetically manipulable control valve for controlling bladder draining, a novel indwelling urethral catheter with incontinence control that can be entirely recessed within the penis in substantially undetectable fashion, a novel indwelling urethral catheter with an incontinence control valve that can be easily actuated with the magnet that is small enough to be carried in a pocket, a novel indwelling urethral catheter with a valve that automatically closes when a magnetic actuating device is moved away from the penis, a novel magnetically actuated valve, and a novel method of draining fluid from a bladder.

Other objects and features of the invention will be in part apparent and in part pointed out hereinafter.

The indwelling urethral catheter with incontinence control, in accordance with one embodiment of the invention, includes a flexible elongated tubular member having a fluid drainage passage. The tubular member has bladder engaging means and a urethra engaging member that cooperate to prevent movement of the tubular member from a predetermined position in the urethra and bladder.

Valve means for controlling incontinence are provided at an opposite end portion of the tubular member to control movement of fluid through the drainage passage. The valve means includes a valve member having a normally closed position. The valve member is magnetically actuatable into an open condition by a small magnetic member held in proximity of the penis.

In a preferred embodiment of the invention, the valve means include a ball valve in axial alignment with a magnetically actuatable member and a valve orifice in a valve seat under the influence of a biasing spring. The magnetically actuatable member is deflected by a magnet that is manually positioned externally of the penis in proximity of the valve means. The external magnet deflects the magnetically actuatable member into a position of misalignment with the valve orifice to permit the ball valve to unseat from the valve seat and enable fluid to flow through the orifice for discharge from the penis.

Removal of the external magnetic member from its location proximate the valve means in the penis enables the valve means to automatically assume its normally closed position.

In one embodiment of the invention the valve seat is at an upstream end of the fluid flow path. When fluid pressure within the fluid drainage passage of the incontinence device builds up to a predetermined pressure, such pressure will operate to unseat the valve ball from the valve seat. Fluid can thus discharge from the penis without valve actuation by the external magnet. Thus the incontinence device has a pressure relief feature that assures discharge of fluid at a pressure level which will not cause damage to the bladder, kidneys or other portions of the urinary system.

In another embodiment of the invention, the valve ball and valve seat are located at a downstream portion of the fluid drainage passage. This embodiment does not include a pressure relief feature and discharge of fluid through the valve always requires actuation of the valve into an open position with the external magnet.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

Figures 1, 2, 3:
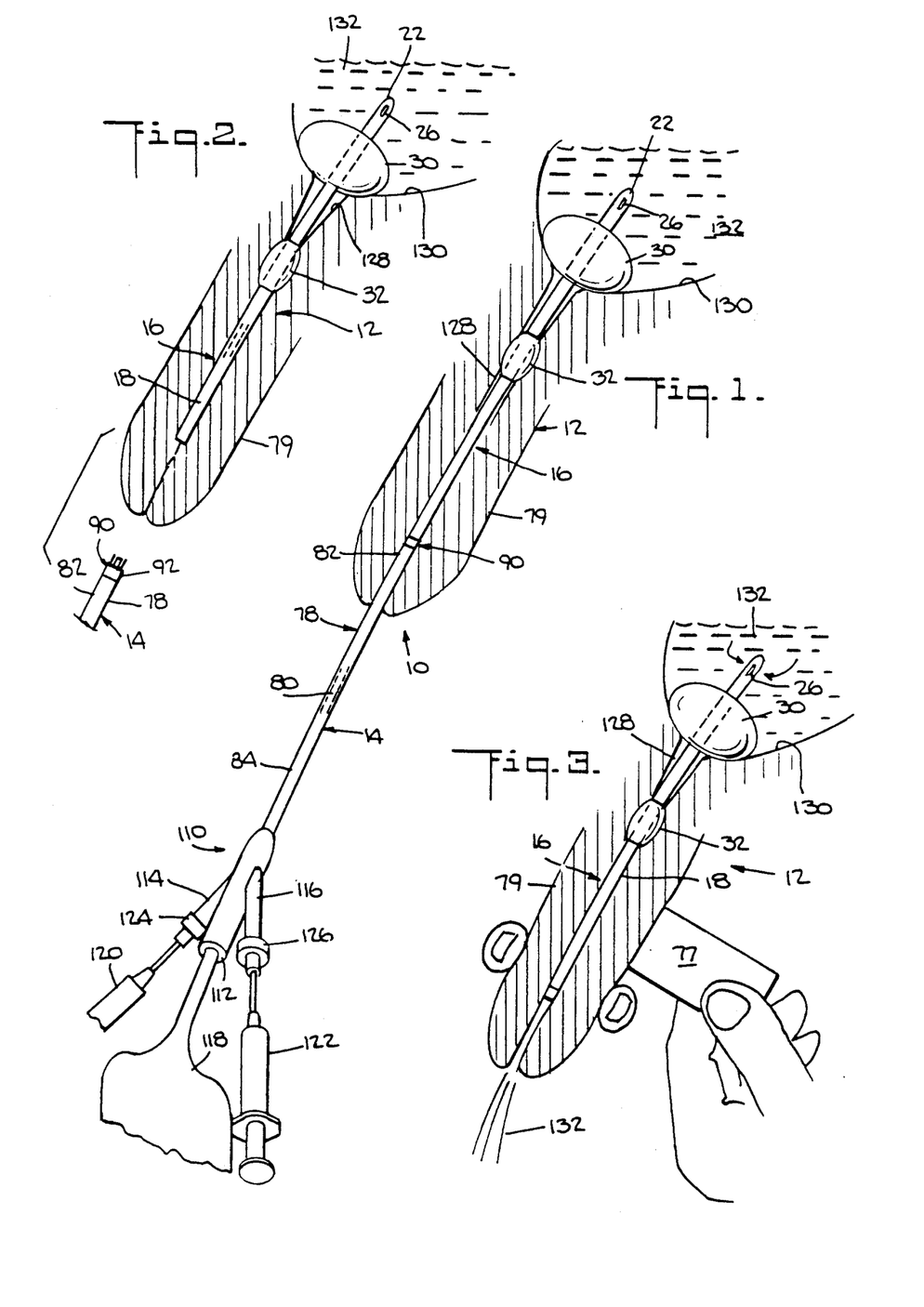
FIG. 1 is a simplified schematic view of the indwelling urethral catheter with incontinence control incorporating one embodiment of the invention, during installation in a penis.
FIG. 2 is a view similar to FIG. 1 with the collection bag and inflation arrangement removed.
FIG. 3 is a view similar to FIG. 2 showing the manner in which the incontinence device is magnetically actuated to permit drainage of fluid from the bladder.

A catheter assembly incorporating one embodiment of the invention is generally indicated by the reference number 10 in FIG. 1.

Referring to FIGS. 4-9, the catheter assembly 10 includes an incontinence portion 12 and an inflation/drainage member 14 adapted to be detachably joined to the incontinence portion 12.

Figures 4, 5, 6:
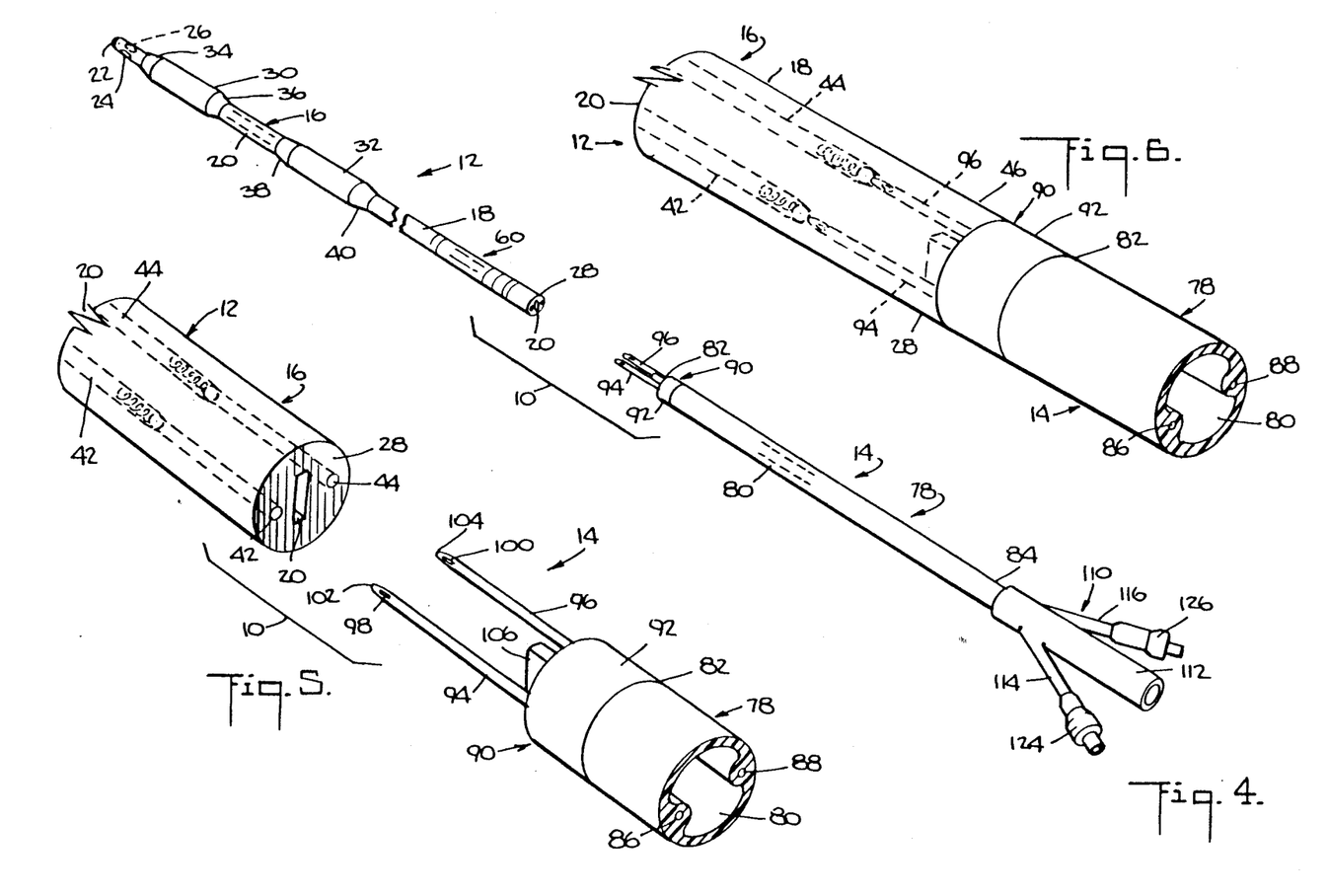
FIG. 4 is a disassembled perspective view of the indwelling urethral catheter with incontinence control prior to installation in the urethral passage and bladder.
FIG. 5 is an enlarged fragmentary perspective view thereof.
FIG. 6 is a view similar to FIG. 5 in assembled condition.
Figure 7:
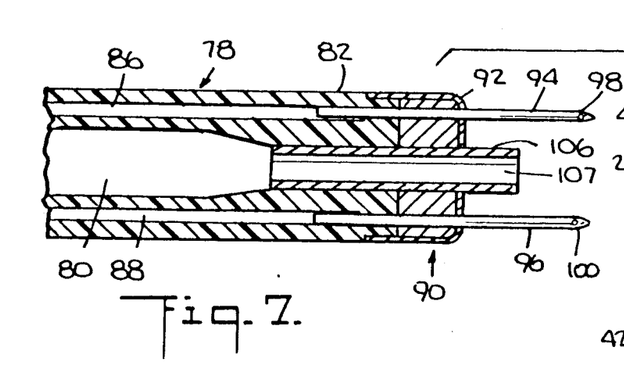
FIG. 7 is an enlarged fragmentary sectional view thereof corresponding to FIG. 5.

The incontinence portion 12 comprises an elongated tubular member 16 which can be formed of silicone. The tubular member 16 has an outside tubular surface 18 and an interior fluid drainage passage 20. The drainage passage 20 extends from an end portion 22 of the tubular member 16 to an opposite end portion 28 thereof. The end portion 22 of the tubular member 16 is provided with oppositely disposed bladder drainage openings 24 and 26 that communicate with the drainage passage 20.

An inflatable bladder balloon 30, preferably formed of silicone is joined to the periphery of the tubular member 16 at a predetermined distance from the end portion 22. An inflatable urethra cuff 32 also formed of silicone is joined to the periphery of the tubular member 16 at a predetermined distance from the bladder balloon 30. The bladder balloon 30 and the urethral cuff 32 are initially deflated as shown in FIG. 4.

Opposite end portions 34 and 36 of the bladder balloon 30 are secured to the outer surface 18 of the tubular member 16 in leak-tight arrangement using a suitable known silicone adhesive. In similar fashion, opposite end portions 38 and 40 of the urethral cuff 32 are secured to the tubular surface 18 of the tubular member 16 in leaktight fashion.

Figure 8:
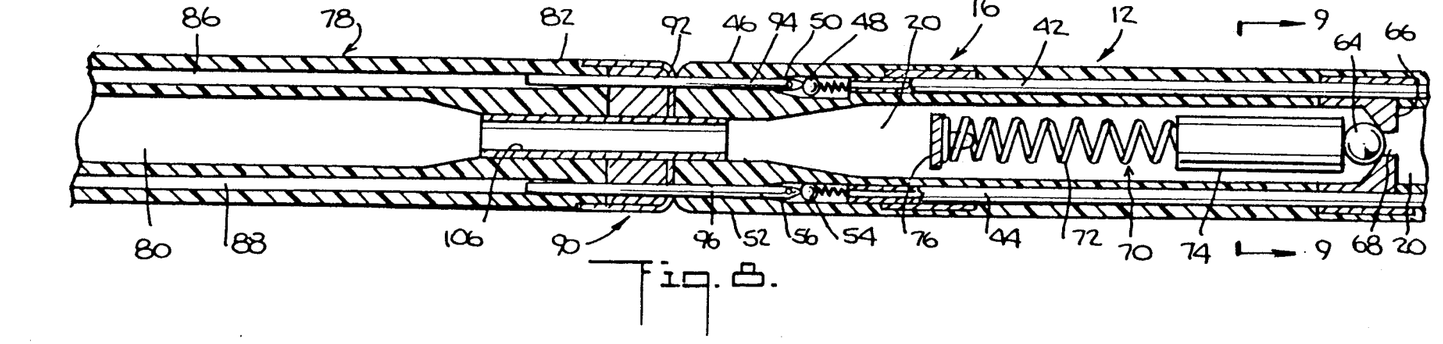
FIG. 8 is an enlarged fragmentary sectional view thereof corresponding to FIG. 6.
Figure 9:
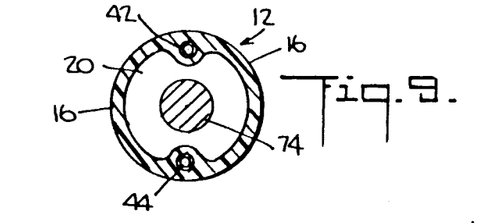
FIG. 9 is a sectional view taken on the line 9—9 of FIG. 8.

As most clearly shown in FIG. 8, a pair of inflation lumen 42 and 44 are formed on the interior of the tubular member 16. The inflation lumen 42, for example, communicates with the bladder balloon 30, and the inflation lumen 44 communicates with the urethral cuff 32.

A distal end portion 46 of the inflation lumen 42 is provided with a spring biased ball valve 48 that is in a normally closed position against a valve seat 50. Similarly the inflation lumen 44 at a distal portion 52 includes a spring biased ball valve 54 that is normally in a closed position against a valve seat 56.

An incontinence valve 60 is provided in the incontinence portion 12 a predetermined distance from the end portion 28 of the tubular member 16.

The incontinence valve 60 includes a ball member 64 normally biased against a valve seat portion 66 having a surface of conical form and a valve orifice 68. The ball member 64 can be formed, for example of stainless steel with gold plating, plastic, silicone or borosilicate glass.

Biasing means 70 for urging the ball member 64 to close the orifice 68 include a biasing spring 72 and a magnetically actuatable member 74 in the form of a cylinder, secured to one end of the biasing spring 72. The biasing spring 70 can be formed of stainless steel (MP35N), monel or any other suitable nonmagnetic spring material.

A spring seat member 76 is provided a predetermined distance from the valve seat 66 for retaining an opposite end of the biasing spring 72. The spring seat 76 can be formed of stainless steel or plastic, for example.

Figures 10, 11:
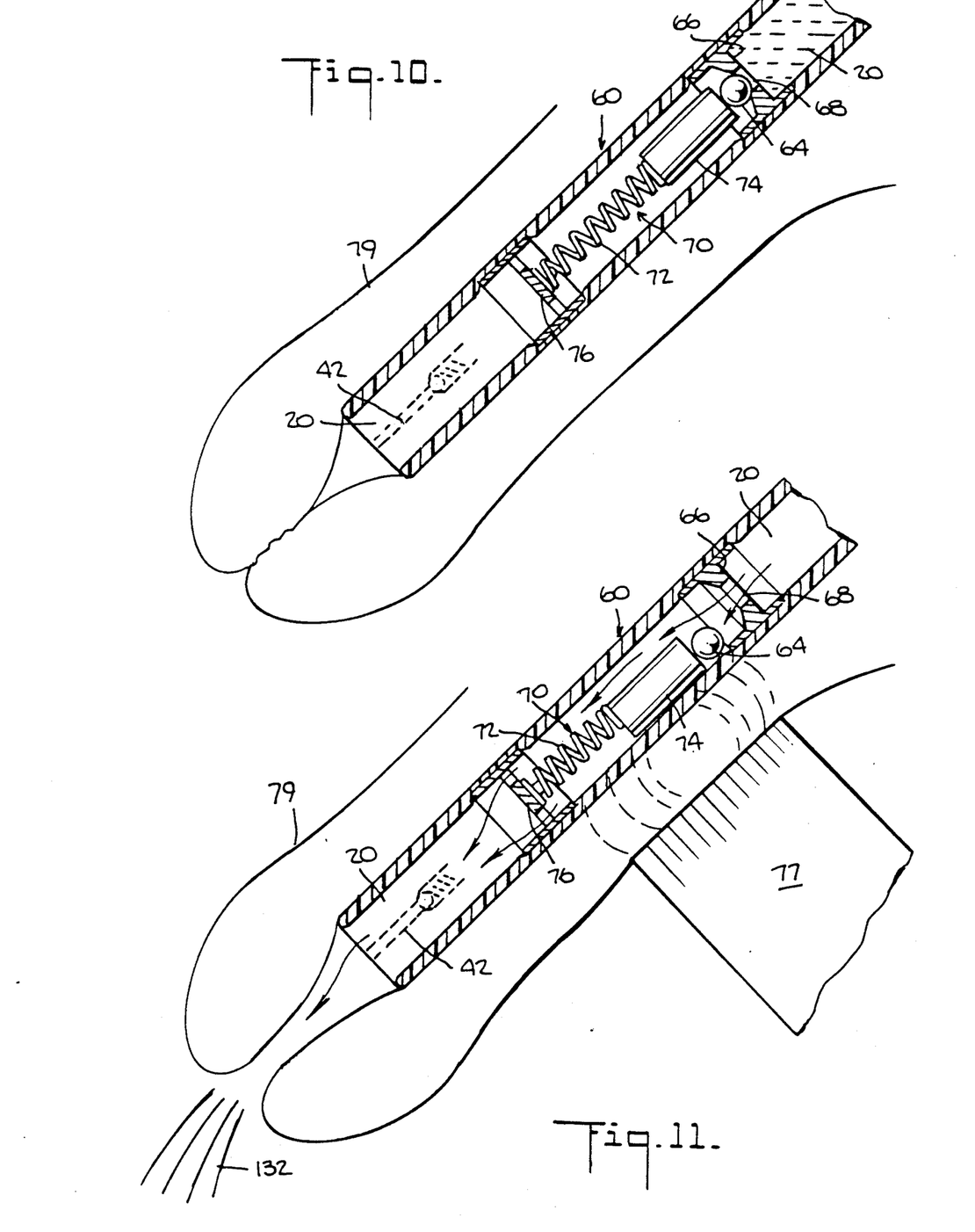
FIG. 10 is an enlarged fragmentary view thereof in operational position with the valve means in a valve closed position.
FIG. 11 is a view similar to FIG. 10 showing the valve means magnetically actuated to an open position to permit fluid flow.
Figures 12, 13:
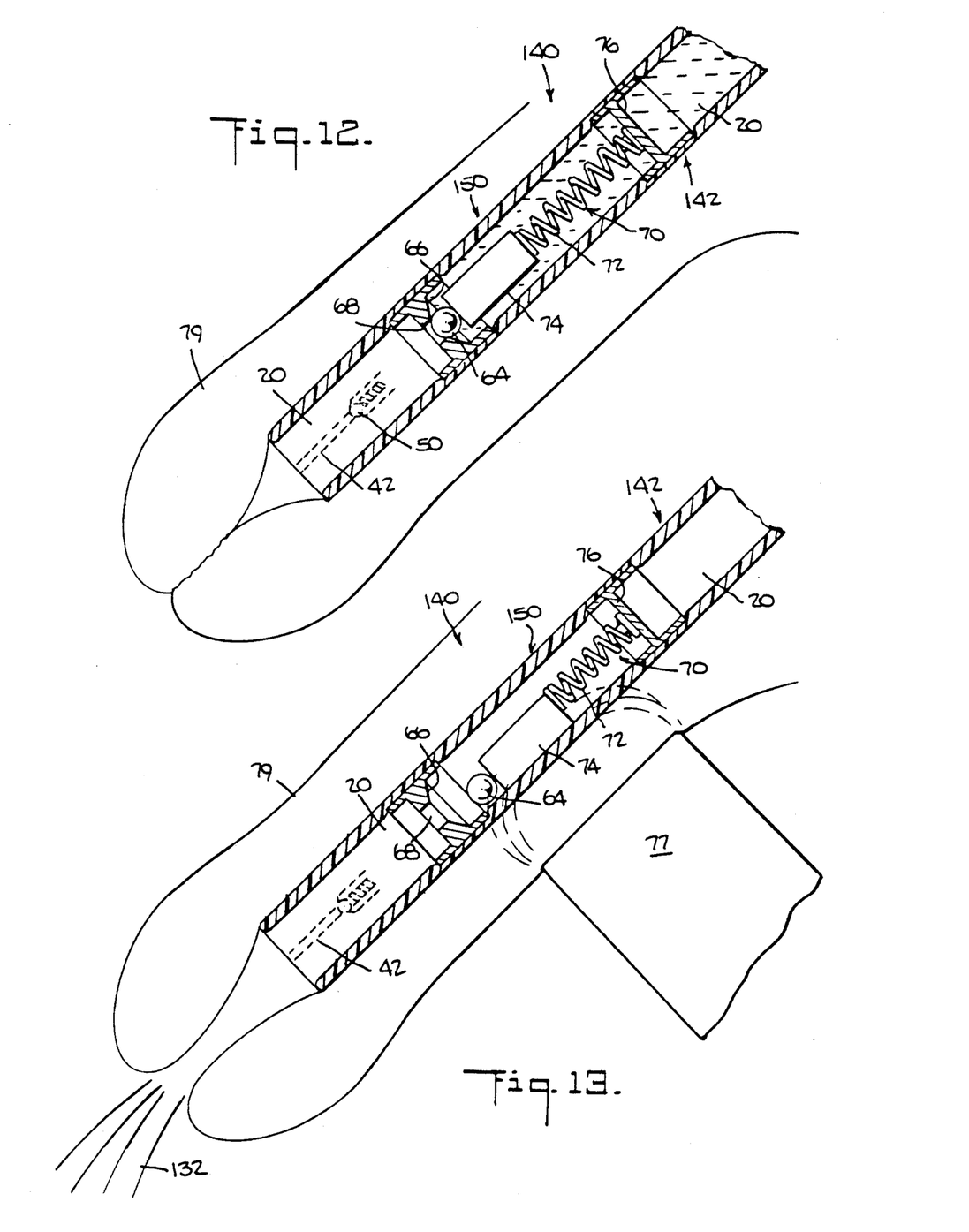
FIGS. 12 and 13 illustrate a further embodiment of the invention in valve closed and valve open positions corresponding to that shown in the embodiments of FIGS. 10 and 11.

The incontinence valve 60, which is in a normally closed position, is actuated to an open condition by an external manually movable magnet 77 (FIGS. 3, 11 and 13). The magnet 77 can be formed of a rare earth magnet such as neodymium-iron-boron or samarium-cobalt. The magnetically actuatable member 74 can also be formed of neodymium-ironboron or samarium-cobalt.

The incontinence valve 60, when normally closed as shown in FIG. 10, prevents fluid from the fluid drainage passage 20 from passing through the valve orifice 68, thus maintaining continence. The biasing spring 72 and the magnetically actuatable member 74 are selected to provide a predetermined biasing force on the ball member 64 that is sufficient to maintain the ball member 64 in a closed position during activities associated with a relatively active individual. Thus there is little likelihood that the ball member 64 would inadvertently unseat from the valve seat 66 as a result of physical activity or movement of the user.

However if fluid pressure in the fluid passage 20 reaches a predetermined level which overcomes the biasing force of the biasing spring 72, the ball member 64 will unseat from the valve seat 66 to permit fluid to flow past the incontinence valve 60 whether or not the magnetically actuatable member 74 is actuated. This result is intended to avoid excess pressure buildup in the bladder which might be harmful to the bladder or other portions of the body such as the kidneys. Thus the incontinence valve 60 provides an automatic pressure relief safety feature wherein the relief pressure is a function of the spring force.

When it is desired to actuate the incontinence valve 60 to an open condition, the magnet 77 is manually placed adjacent the penis 79 as shown in FIG. 11, thereby attracting (or repelling) the magnetically actuatable member 74 from the position of FIG. 10. Movement of the magnetically actuatable member 74 from its position of alignment with the ball 64 and the orifice 68 enables the ball 64 to unseat from the valve seat 66 and permit fluid to flow through the orifice in the manner shown in FIG. 11.

The magnetically actuatable member 74 and the ball member 64 are sized such that the ball cannot pass between the magnetically actuatable member 74 and the wall of the tubular member 16. Thus for all possible deflections of the magnetically actuatable member 74 the ball member 64 is always retained between the free end portion of the magnetically actuatable member 74 and the valve seat 66. When the manually movable magnet 77 is withdrawn from proximity to the incontinence valve 60, the biasing spring 72 and the magnetically actuatable member 74 urge the ball member 64 against the valve seat 66 into the normally closed position wherein the ball member 64 closes the orifice 68.

The externally movable magnet 77 is preferably of a size that is unobtrusive and can be stored in a pocket, such as for example, 1 inch ×3 inches ×3/16 inches thick. If desired, the externally movable magnet 77 can be sheathed in a bag or container that is nonmagnetic.

The inflation/drainage member 14 comprises a drainage duct member 78 having an interior duct passage 80 that extends from an end portion 82 (FIG. 4) to an opposite end portion 84. The drainage duct member can be formed of silicone, polyvinyl chloride, or any other suitable known biocompatible thermoplastic.

A pair of inflation lumen 86 and 88 (FIGS. 5-8) corresponding to the inflation lumen 42 and 44 are formed on the inner surface of the duct passage 80.

An engagement assembly 90 formed of a suitable plastic or metal such as stainless steel, includes a cap portion 92 adapted to form a leak-tight seal around the end portion 82 of the drainage duct member 78. A pair of inflation needles 94 and 96, having respective inflation openings 98 and 100, extend longitudinally from the cap portion 92. The inflation needles 94 and 96 align with and form a continuation of the inflation lumen 86 and 88. Blunt ends 102 and 104 are formed at the respective free ends of the inflation needles 94 and 96.

A duct extension piece 106 which can be formed of plastic or stainless steel, projects from the cap portion 92 intermediate the inflation needles 94 and 96. The duct extension 106 defines a duct extension passage 107 that is a continuation of the duct passage 80 and is of complementary cross section with the drainage passage 20 at the distal end 28 of the tubular member 16.

A branch member 110 (FIGS. 1 and 4) joins the end portion 84 of the drainage duct member 78 and includes a drainage extension 112 that communicates with the duct passage 80. The branch member 110 also includes syringe receivers 114 and 116 that respectively communicate with the inflation lumen 86 and 88.

In using the catheter assembly 10, the inflation/drainage member 14 is joined to the incontinence portion 12 by aligning the inflation needles 94 and 96 with the lumen portions 42 and 44 of the tubular member 12 as shown in FIG. 5. A free end portion of the duct extension 106 will thus be received in the fluid passage 20 downstream from the incontinence valve 60 as the inflation needles 94 and 96 are received in the lumen portions 42 and 44 for engagement in the manner shown in FIGS. 6 and 8. The periphery of the tubular member 12 is substantially identical to the periphery of the cap portion to provide a smooth continuous surface where the tubular member 12 and the engagement assembly 90 join.

The inflation needles 94 and 96, as they pass into the distal ends 46 and 52 of the lumen portions 42 and 44, unseat the respective balls 48 and 54 from their respective valve seats 50 and 56 for entry into the inflation lumens 42 and 44 of the tubular member 16 as shown in FIG. 8.

A collection bag 118 (FIG. 1) is connected to the drainage extension 112 and respective syringes 120 and 122 are positioned in the syringe receivers 114 and 116 with appropriate predetermined amounts of a suitable known inflation fluid.

After the incontinence portion 12 and the inflation/drainage member 14 are joined together, a suitable known lubricant (not shown) is applied to the tubular surface 18 of the tubular member 16. The tubular member 16 is inserted into the urethra 128 to position the uninflated bladder balloon 30 in the bladder 130. The tubular member 16 is sized such that the incontinence valve 60 substantially aligns with the penile meatus. Tubular members 16 of various different lengths can be inventoried to ensure such alignment with the penile meatus.

With the uninflated bladder balloon 30 thus positioned in the bladder 130, the syringes 120 and 122 can be operated to force fluid through the respective lumen passages 86-42 and 88-44 to inflate the bladder balloon 30 and the urethral cuff 32 in the manner shown in FIG. 2.

When inflation is completed, the syringes 120 and 122 are removed and self-sealing valves 124 and 126 provided on the syringe receivers 114 and 116 ensure that the inflation volume of the bladder balloon 30 and the urethral cuff 32 is maintained.

Bladder fluid 132 (FIG. 4) is thus enabled to pass into the openings 24 and 26 for passage through the fluid drainage passage 20, into the duct extension passage 107 and through the duct passage 80 into the collection bag 118. There is no communication between the fluid passages 20, 107, 80 and the inflation lumens 42, 44 and 86, 88.

Under this arrangement, bladder fluid 132 can be continuously drained from the bladder 130 past the incontinence valve 60 into the collection bag 118, provided the external magnet 77 is maintained proximate the penis, in any suitable manner, such as for example, in a truss-like arrangement (not shown) which holds the magnet 77 proximate the penis. If continuous drainage is not desired but the collection bag 118 is to be used, the incontinence valve 60 is maintained in the normally closed position and operated using the magnet 77 in the manner previously described. The filled collection bag 118 can be emptied or replaced as needed.

When it is feasible for a patient to control his own bladder drainage without the collection bag 118, the inflation/drainage member 14 is detached from the incontinence portion 12 in the manner shown in FIG. 2. Thus the patient can manually control bladder drainage by selectively opening the incontinence valve 60 using the magnet 77.

As the inflation/drainage member 14 is separated from the incontinence portion 12, the inflation needles 94 and 96 are withdrawn from the lumen 42 and 44 and the spring biased ball valves 48 and 54 assume their normally closed positions. Inflation volume of the bladder balloon 30 and urethral cuff 32 is thus maintained.

As bladder fluid 132 accumulates in the bladder 130 to a point where bladder drainage is desired, the patient manually holds the magnet 77 adjacent the penis in the manner shown in FIG. 11. The magnet 77 need not be accurately located since it has sufficient flux to open the valve 60 when placed alongside the penis near the penile meatus.

When bladder drainage is completed, removal of the magnet 77 from the area of the penile meatus enables the valve 60 to reassume its normally closed position thereby shutting off the fluid drainage passage 20 and allowing bladder fluid 132 to accumulate in the bladder 130.

A patient can thus control and limit bladder discharge as he chooses. As will be apparent, the incontinence portion 12 which permits such control is entirely recessed in the penis and substantially undetectable.

If there is a need to remove the incontinence portion 12 from the urethra 128, the penis is collapsed against the pubis, exposing the distal end of the incontinence portion 12. The tube member 16 is cut just proximal to the valves 48 and 54 to enable the bladder balloon 30 and the urethral cuff 32 to deflate. The incontinence portion 12 can then be removed.

Another embodiment of the catheter assembly is generally indicated by the reference number 140 in FIGS. 12 and 13. The catheter assembly 140, which includes an incontinence portion 142, does not have a pressure relief feature and is structurally identical to the catheter assembly 10 except for the orientation of an incontinence valve 150 in the incontinence portion 142.

The incontinence valve 150 includes components that are identical to the incontinence valve 60. However the valve seat 66 and the ball member 64 are at a downstream flow portion of the tubular member 16.

Under this arrangement the accumulation of bladder fluid 132 in the fluid drainage passage 20 tends to maintain the ball 64 in its closed position on the valve seat 66. Actuation of the incontinence valve 150 into an open position requires placement of the manually movable magnet 77 in proximity of the valve 150 as shown in FIG. 13. Operation of the valve 150 is in all other respects similar to operation of the valve 60.

Accordingly, placement of the magnet 77 proximate the valve 150 causes the magnetically actuatable member 74 to deflect from its alignment with the orifice 68. Once the magnetically actuatable member 74 is so deflected, the ball member 64 is no longer stably positioned against the orifice 68 and fluid within the fluid drainage passage 20 unseats the ball and flows through the orifice 68 for discharge from the penis as shown schematically in FIG. 13.

Removal of the magnet 77 from its position adjacent the penis enables the biasing spring 72 to urge the magnetically actuatable member 74 toward the orifice 68 and confine the ball member 64 against the orifice 68. Flow of fluid through the drainage passage 20 thus ceases without magnetic actuation of the magnetically actuatable member 74.

Installation and operation of the catheter assembly 140 with the inflation/drainage member 14 is accomplished in a manner similar to that previously described for the catheter assembly 10.

It should be noted that other suitable known means of anchoring the incontinence portions 12 and 142 in the bladder such as non-inflatable spirals and malecot portions can be used, and other suitable known non-inflatable cuff arrangements can be used for preventing migration of the incontinence portions 12 and 142 in the urethra.

Some advantages of the invention evident from the foregoing description include a urethral indwelling catheter with incontinence control that provides the option of continuous bladder drainage as well as the option of user controlled bladder drainage. Either option can be obtained with just one installation of a catheter assembly in the urethra and bladder.

A further advantage is that the valve means for controlling movement of fluid from the bladder can be magnetically actuatable by a small, relatively innocuous magnet that is no larger than a small key case and can be easily carried around by the user. A further advantage is that the incontinence valve does not require manual manipulation of the penis to actuate the valve. Such manual manipulation can cause discomfort and may require manual dexterity. Use of the present magnetic device requires little manual dexterity, and does not require manipulation of the penis to actuate the incontinence valve and thus does not cause discomfort.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A urethral catheter for controlling incontinence in males comprising a flexible elongated tubular member having first and second opposing end portions, said end portions each having an opening, said tubular member having a drainage passage extending between said openings, said tubular member being predeterminedly dimensioned so as to be positionable indwelling within the male urethra with said first end portion at least proximate to the bladder and said second end portion in the pendulous penis, valve means in said second end portion of said tubular member for controlling fluid flow through said drainage passage, said valve means having a normally closed position for preventing flow of fluid through said drainage passage, said valve means being magnetically actuatable into an open condition by a magnet placed external to the pendulous penis proximate to said valve means for permitting flow through said drainage passage, and retaining means secured to said tubular member for retaining said indwelling tubular member within the urethra.

2. The urethral catheter as claimed in claim 1 wherein said valve means includes a movable valve member, a valve seat engageable by said valve member and biasing means for biasing said valve member into engagement with said valve seat when said valve means is in said normally closed position.

3. The urethral catheter as claimed in claim 2 further comprising a magnet for imposing a magnetic deflection force on said biasing means to unseat said valve member from said valve seat thereby placing said valve means into an open condition, said biasing means reseating said valve member upon removal of said magnetic deflection force.

4. The urethral catheter as claimed in claim 2 further comprising actuating means for imposing a magnetic deflection force on said magnetically actuatable member to deflect said magnetically actuatable from said first nondeflected position to place said valve in an open condition, and wherein removal of said magnetic deflection force enables said biasing means to automatically urge said valve member into said normally closed position.

5. The urethral catheter as claimed in claim 2 wherein said biasing means includes a spring having a fixed end portion and a deflectable end portion.

6. The urethral catheter as claimed in claim 2 wherein said biasing means includes a magnetically actuatable member having a first predetermined location relative to said valve seat when said valve member is in said closed position and magnetically movable away from said first predetermined location relative to said valve seat when said valve member is in said open condition.

7. The urethral catheter as claimed in claim 6 wherein said magnetically actuatable member is a first predetermined distance from said valve seat when said valve member is in said closed position and a second predetermined distance greater than said first predetermined distance from said valve seat when said valve member is in said open condition.

8. The urethral catheter as claimed in claim 2 wherein said valve means includes a longitudinal axis and a magnetically actuatable member, said magnetically actuatable member being in axial alignment with said valve seat when said valve member is in said closed position, said magnetically actuatable member being out of axial alignment with said valve seat when said valve member is in said open condition.

9. The urethral catheter as claimed in claim 6 wherein said magnetically actuatable member is formed of a magnetic or magnetically attractive material.

10. The urethral catheter as claimed in claim 6 wherein said magnetically actuatable member is in a general shape of a cylinder.

11. The urethral catheter as claimed in claim 9 wherein said magnetically actuatable member includes opposite ends and said biasing means further include a spring having opposite ends, one end of said magnetically actuatable member being in contact with one end of said spring, the other end of said spring having a fixed position in said valve means, and the other said end of said magnetically actuatable member being engageable with said valve member.

12. The urethral catheter as claimed in claim 11 wherein said valve member is a ball.

13. The urethral catheter as claimed in claim 6 wherein said magnetically actuatable member includes opposite ends and said biasing means further include a spring having opposite ends, one end of said magnetically actuatable member being in contact with one end of said spring, the other end of said spring having a fixed position in said valve means, and the other said end of said magnetically actuatable member being engageable with said valve member.

14. The urethral catheter as claimed in claim 13 wherein said valve member is a ball.

15. The urethral catheter as claimed in claim 2 wherein said valve member is oriented in said tubular member such that the normal path of fluid flow through the tubular member is in a direction from the valve seat to the valve member.

16. The urethral catheter as claimed in claim 2 wherein said valve means is oriented in said tubular member such that the normal path of fluid flow through the tubular member is in a direction from the valve member to the valve seat.

17. A method of draining fluid from the male urinary system comprising (a) installing a predeterminedly dimensioned catheter in the urethra so as to extend from the bladder into the pendulous penis, (b) incorporating a magnetically actuatable, externally controllable valve in the catheter so as to be positioned within the pendulous penis when said catheter is installed, said valve having a normally closed feature such that the valve requires actuation to an open condition to permit bladder drainage through the catheter, (c) actuating the valve to an open condition with a magnet placed totally external to and in proximity of the pendulous penis, and (d) removing the magnet from proximity of the pendulous penis to permit the valve to reassume its normally closed condition.

18. A urethral catheter for controlling incontinence in males comprising (a) a flexible elongated tubular member having a fluid drainage passageway, said tubular member being predeterminedly dimensioned so as to be insertable and properly positionable within the urethra with one end at least proximate to the bladder and the other end in the pendulous penis, (b) a valve within said tubular member proximate to said other end so as to be within the pendulous penis when said tubular member is properly positioned, said valve including (i) a valve seat with an orifice, (ii) a valve member removably engageable with said valve seat, said valve member being in a closed position when engaged with said valve seat and closing said orifice, said valve member being in an open condition when unseated from said valve seat and an opening said orifice, (iii) biasing means for urging said valve member into engagement with said valve seat to normally maintain said valve member in said closed position, (iv) said biasing means including a deflectable magnetically actuatable member having a first nondeflected position corresponding to said closed position of said valve member and a deflected position corresponding to an open condition for said valve member, (c) actuating means operable totally external to the body and removably positionable proximate to the pendulous penis for imposing when proximate to the pendulous penis a magnetic deflection force on said magnetically actuatable member for deflecting said magnetically actuatable member from said first nondeflected position and placing said valve in said open condition, and for removing said imposed magnetic deflection force when distant from the pendulous penis enabling said biasing means to automatically urge said valve member into said normally closed position, and (d) retaining means secured to said tubular member for retaining said tubular member within the urethra.

* * * * *